(12) United States Patent
Ebben et al.

(10) Patent No.: US 6,704,392 B2
(45) Date of Patent: Mar. 9, 2004

(54) X-RAY TUBE AND METHOD HAVING TILTED ROTATION AXIS

(75) Inventors: Thomas G. Ebben, Sullivan, WI (US); Douglas J. Snyder, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 237 days.

(21) Appl. No.: 09/898,760

(22) Filed: Jul. 3, 2001

(65) Prior Publication Data

US 2003/0072408 A1 Apr. 17, 2003

(51) Int. Cl.[7] ................................................. H01J 35/10
(52) U.S. Cl. ...................................................... 378/144
(58) Field of Search ............................ 378/144, 16, 15

(56) References Cited

U.S. PATENT DOCUMENTS

| | | | | |
|---|---|---|---|---|
| 4,523,327 A | * | 6/1985 | Eversole | 378/144 |
| 5,907,592 A | * | 5/1999 | Levinson | 378/144 |
| 6,229,869 B1 | * | 5/2001 | Hu | 378/15 |
| 6,332,013 B1 | * | 12/2001 | Hsieh | 378/15 |

* cited by examiner

*Primary Examiner*—Harshad Patel
(74) *Attorney, Agent, or Firm*—Foley & Lardner

(57) ABSTRACT

A computed tomography system comprises a gantry and an x-ray tube. The gantry rotates about a gantry axis of rotation. The x-ray tube is mounted to the gantry, and comprises a rotatable assembly having a tube axis of rotation. The tube axis of rotation is angularly displaced from the gantry axis of rotation by a tilt angle. Rotation of the x-ray tube about the gantry axis of rotation produces a first moment, and rotation of the rotatable assembly about the tube axis of rotation produces a second moment that opposes the first moment.

38 Claims, 9 Drawing Sheets

X-RAY TUBE AND METHOD HAVING TILTED ROTATION AXIS

FIELD OF THE INVENTION

The present invention relates generally to x-ray tubes. More particularly, the present invention relates to systems and methods for balancing mechanical loads in x-ray tubes.

BACKGROUND OF THE INVENTION

X-ray tubes have found widespread application in devices such as imaging systems. X-ray imaging systems utilize an x-ray tube to emit an x-ray beam which is directed toward an object to be imaged. The x-ray beam and the interposed object interact to produce a response that is received by one or more detectors. The imaging system then processes the detected response signals to generate an image of the object.

For example, in computed tomography (CT) imaging, an x-ray tube projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated radiation beam received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third-generation CT systems, the x-ray tube and the detector array are rotated with a gantry within the imaging plane and around the object to be imaged so that the angle at which the x-ray beam intersects the object constantly changes. A group of x-ray attenuation measurements, i.e. projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two-dimensional slice taken through the object.

Typically, an x-ray tube comprises a vacuum vessel, a cathode assembly, and an anode assembly. The vacuum vessel is typically fabricated from glass or metal, such as stainless steel, copper or a copper alloy. The cathode assembly and the anode assembly are enclosed within the vacuum vessel.

To generate an x-ray beam, the cathode is heated to a temperature at which the cathode begins to emit electrons. A voltage difference (typically, in the range of 60 kV to 140 kV) is maintained between the cathode and anode assemblies and accelerates the electrons, causing the electrons to impact a target zone of the anode at high velocity. Upon impact, a small fraction (less than 1%) of the kinetic energy of the electrons is converted to high energy electromagnetic radiation, or x-rays, while the balance produces heat. The x-rays emanate from a focal spot of the target zone in all directions, and a collimator is then used to direct x-rays out of the vacuum vessel in the form of an x-ray beam toward the patient.

In the first x-ray tube designs, the anode assembly remained stationary. However, due to the large amount of heat that is produced (the focal spot of the anode can reach temperatures of about 2700° C.), a rotating anode design has been adopted for many applications. According to this design, the anode assembly includes a rotating disk and the focal spot moves along a target track on the anode. This prevents material on the anode from melting, in a manner generally analogous to the manner in which waiving one's hand over a candle rather than holding one's hand directly over the candle prevents one's hand from burning.

Although the rotating anode design is advantageous in that it promotes heat dissipation, the rotating anode design provides additional challenges inasmuch as two rotating systems are employed. Specifically, the x-ray tube comprises a rotating anode assembly that rotates within the x-ray tube about a tube axis of rotation, and the x-ray tube itself is mounted to a gantry which is rotating about a gantry axis of rotation (e.g., which may be aligned with a patient).

A difficulty that has been encountered is uneven loading of bearings that support the rotating anode assembly. Rotating anode assemblies have used a cantilevered design in which the rotating disk is mounted at one end of a rotating shaft, with the other end of the rotating shaft being supported by two or more bearing assemblies. As the x-ray tube rotates about the gantry axis of rotation, the resultant centrifugal force that is applied to the x-ray tube is opposed primarily by the bearing assembly that is closer to the rotating disk (closer to the center of gravity), resulting in uneven loading. This is undesirable because it causes premature failure of the bearing assemblies, especially the bearing assembly that provides primary opposition to the centrifugal force caused by rotation of the gantry.

In order to improve performance characteristics of CT systems, it is desirable to increase the gantry rotational speeds that are employed. Increased speeds, however, increase the bearing loads since centrifugal force is proportional to the square of the gantry rotational speed. Therefore, the inability to obtain increased gantry speeds without premature bearing failure has become a limiting factor in the development of CT systems.

Therefore, an improved x-ray tube and method of balancing mechanical loads in an x-ray tube would be highly advantageous.

BRIEF SUMMARY OF THE INVENTION

In a first preferred aspect of the invention, a computed tomography system comprises a gantry and an x-ray tube. The gantry rotates about a gantry axis of rotation. The x-ray tube is mounted to the gantry, and comprises a rotatable assembly having a tube axis of rotation. The tube axis of rotation is angularly displaced from the gantry axis of rotation by a tilt angle. Rotation of the x-ray tube about the gantry axis of rotation produces a centrifugal force that is applied to the x-ray tube. Rotation of the rotatable assembly about the tube axis of rotation produces a gyroscopic moment that results in an additional force being applied to the rotatable assembly that opposes the centrifugal force.

In a second preferred aspect, a method of operating a computed tomography system comprises producing a first moment that acts upon an x-ray tube, and producing a second moment that acts upon the x-ray tube while the first moment is being produced. The x-ray tube being mounted to the gantry. The first moment is produced by rotation of a gantry about a gantry axis of rotation at a gantry rotational speed. The second moment is produced by rotation of a rotating assembly of the x-ray tube about a tube axis of rotation. The tube axis of rotation is tilted with respect to the gantry axis of rotation. The second moment is a gyroscopic moment that is produced by precession of the rotatable assembly. The precession occurs by way of the rotation of the x-ray tube about the gantry axis of rotation and the rotation of the rotatable assembly about the tube axis of rotation. The tube axis of rotation of the rotatable assembly defines an outer surface of a portion of a cone as the rotatable assembly rotates about the gantry axis of rotation.

In a third preferred aspect, a computed tomography system comprises a gantry and an x-ray tube. The gantry rotates about a gantry axis of rotation. The x-ray tube is mounted to the gantry, and comprises a rotatable assembly having a tube axis of rotation. The tube axis of rotation is angularly displaced from the gantry axis of rotation by a tilt angle. Rotation of the x-ray tube about the gantry axis of rotation produces a first moment, and rotation of the rotatable assembly about the tube axis produces a second moment that opposes the first moment.

Advantageously, in the preferred embodiments, the tilt angle causes a gyroscopic moment to be produced which can be used to balance loading in the x-ray tube. Therefore, although it has long been assumed that the tube axis of rotation and the gantry axis of rotation must be parallel, it has surprisingly been found that this is not necessarily the case and that in fact introducing a tilt angle can have significant benefits.

Other principle features and advantages of the present invention will become apparent to those skilled in the art upon review of the following drawings, the detailed description, and the appended claims.

DETAILED DESCRIPTION OF THE INVENTION

Figure 1:
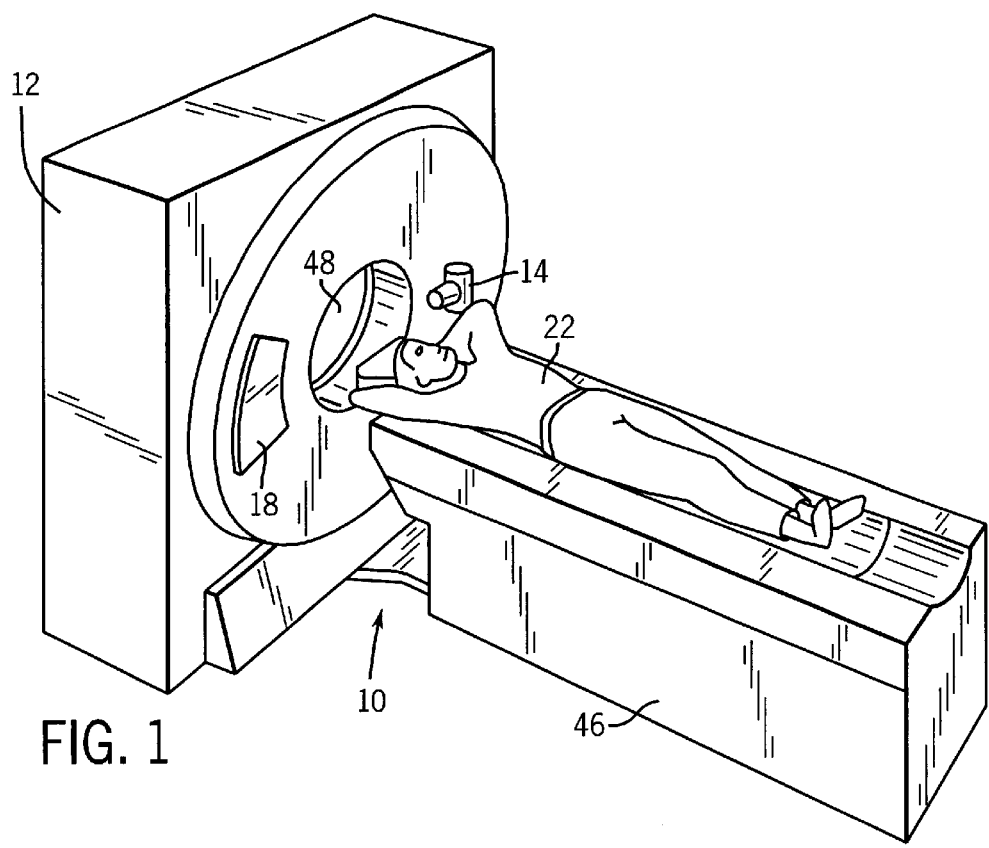
FIG. 1 is a pictorial view of a CT imaging system.
Figure 2:
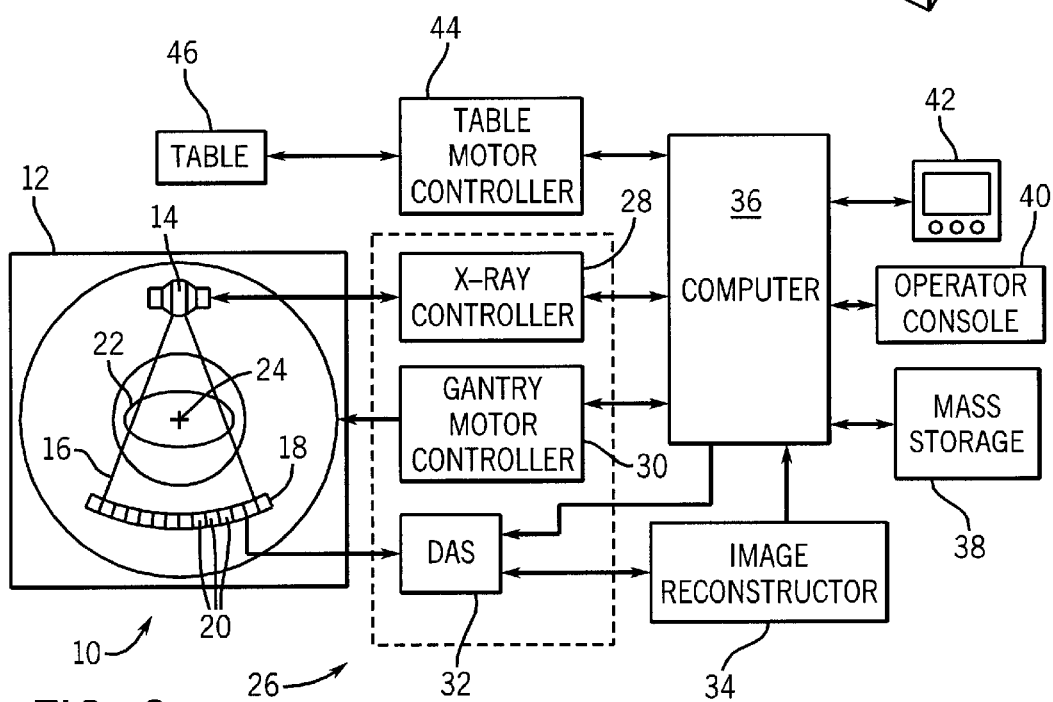
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. An x-ray tube 14 is mounted to the gantry 12 and generates a beam of x-rays 16 that is projected toward a detector array 18 mounted to an the opposite side of gantry 12. X-ray beam 16 is collimated by a collimator (not shown) to lie within an X-Y plane of a Cartesian coordinate system and generally referred to as an "imaging plane". Detector array 18 is formed by detector elements 20 which together sense the projected x-rays that pass through an object 22 such as a medical patient. Detector array 18 may be a single-slice detector or a multi-slice detector. Each detector element 20 produces an electrical signal that represents the intensity of an impinging x-ray beam as it passes through patient 22. During a scan to acquire x-ray projection data, gantry 12 and the components mounted thereon rotate about a gantry axis of rotation 24.

Rotation of gantry 12 and the operation of x-ray tube 14 are governed by a control mechanism 26 of CT system 10. Control mechanism 26 includes an x-ray controller 28 that provides power and timing signals to x-ray tube 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator-supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 along a Z-axis through gantry opening 48.

Figure 3:
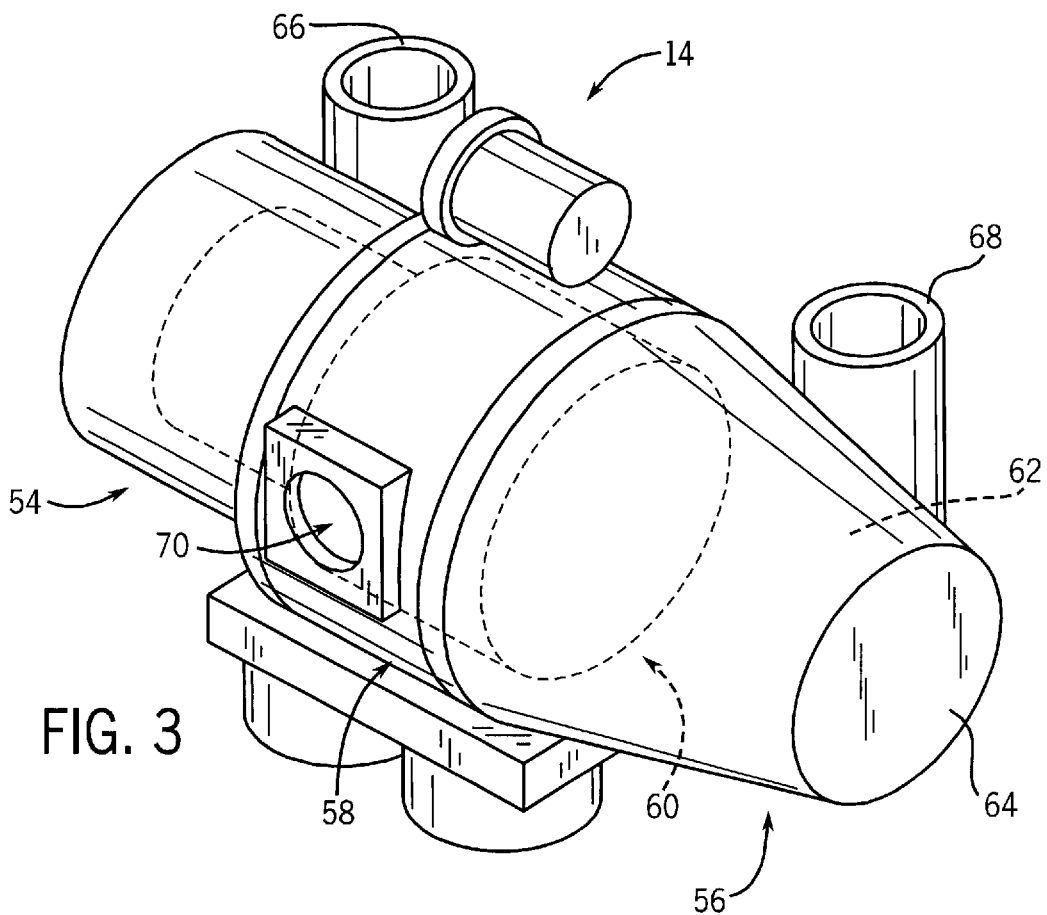
FIG. 3 is a perspective view of a casing enclosing an x-ray tube insert.

FIG. 3 illustrates the x-ray tube 14 in greater detail. The X-ray tube 14 includes an anode end 54, cathode end 56, and a center section 58 positioned between anode end 54 and cathode end 56. The X-ray tube 14 includes an X-ray tube insert 60 which is enclosed in a fluid-filled chamber 62 within a casing 64.

Electrical connections to x-ray tube insert 60 are provided through an anode receptacle 66 and a cathode receptacle 68. X-rays are emitted from x-ray tube 14 through a casing window 70 in casing 64 at one side of center section 58.

Figure 4:
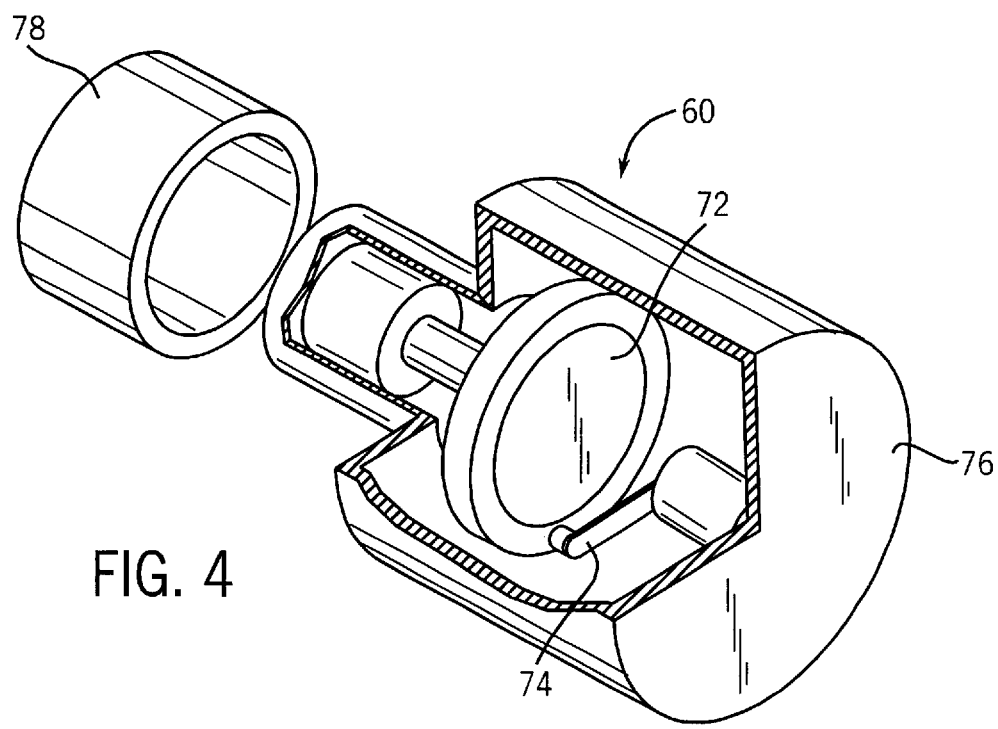
FIG. 4 is a sectional perspective view with the stator exploded to reveal a portion of an anode assembly of the x-ray tube insert of FIG. 3.

As shown in FIG. 4, the x-ray tube insert 60 includes a target anode assembly 72 and a cathode assembly 74 disposed in a vacuum within a vacuum vessel 76. A stator 78 is positioned over vessel 76 adjacent to anode assembly 72. Upon the energization of the electrical circuit connecting anode assembly 72 and cathode assembly 74, which produces a potential difference of, e.g., 60 kV to 140 kV, electrons are directed from cathode assembly 74 to anode assembly 72. The electrons strike target anode assembly 72 and produce high frequency electromagnetic waves, or x-rays, and residual thermal energy. The x-rays are directed out through the casing window 70, which allows the x-rays to be directed toward the object being imaged (e.g., the patient).

Figure 5:
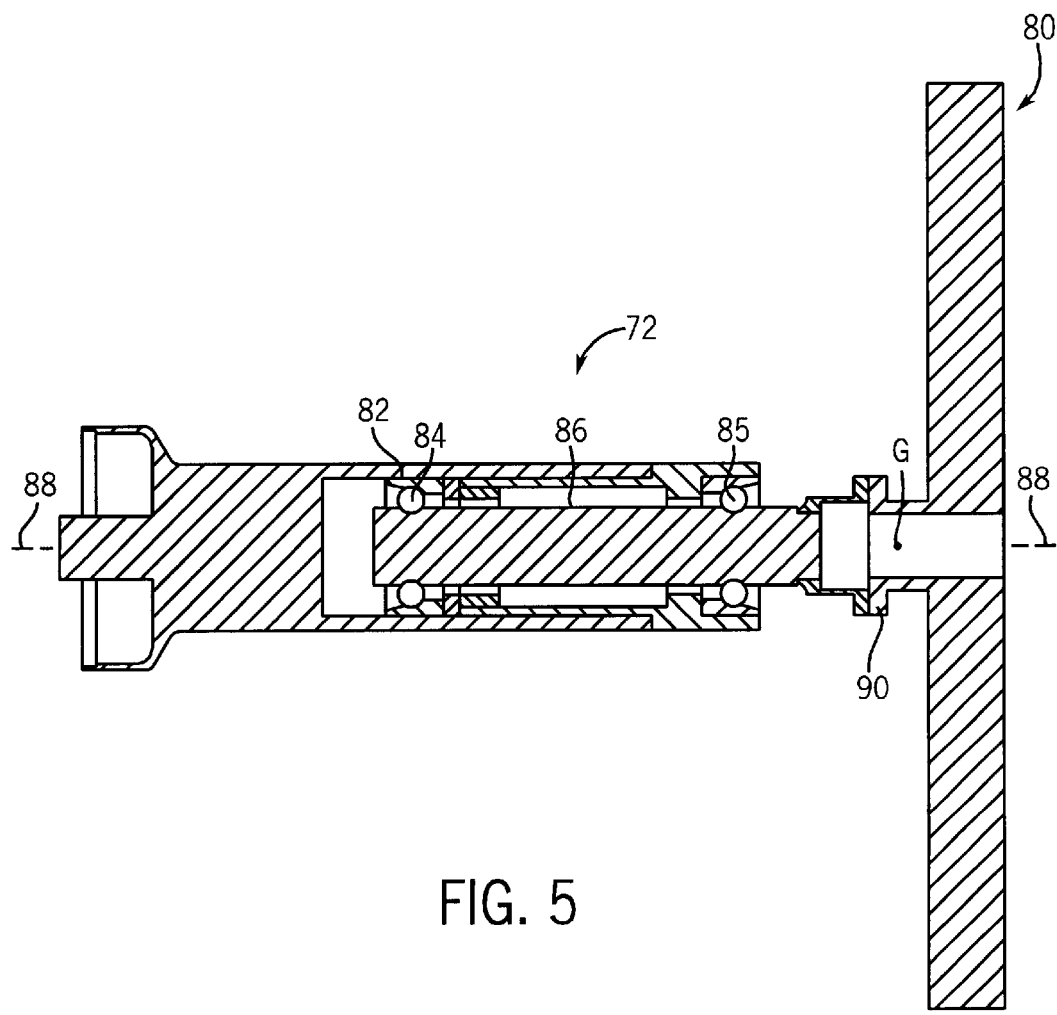
FIG. 5 is a more detailed view of the anode assembly of FIG. 3.

FIG. 5 illustrates a cross-sectional view of the anode assembly 72. The anode assembly 72 includes a target 80, a bearing support 82, a rear bearing assembly 84, and a front bearing assembly 85. The target 80 is a metallic disk made of a refractory metal with graphite possibly brazed to it. The target 80 provides a surface against which electrons from the cathode assembly 74 strike. In the exemplary embodiment, the target 80 rotates by the rotation of a bearing shaft 86. The rotation of the target 80 distributes the area on the target 80 which is bombarded by the electrons.

The bearing support 82 is a cylindrical tube which provides support for the target anode assembly 72. The rear bearing assembly 84 and the front bearing assembly 85 are located within bearing support 82. The target 80 is coupled to a bearing shaft 86 and rotates with the bearing shaft 86 about a tube axis of rotation 88. The target 80 and the bearing shaft 86 in combination form a rotatable assembly 90 that has a center of gravity G which is located between (1) the target 80 and (2) the rear and front bearing assemblies 84 and 85. Thus, disposed along the tube axis of rotation 88 are, in order, the rear bearing assembly 84, the front bearing assembly 85, the center of gravity G and the target 80.

During an imaging operation, the human patient 22 is received inside the gantry 12, and the x-ray tube 14 emits x-rays that pass through the human patient 22 and that are received at the detector array 18. This occurs as the gantry 12 rotates about the gantry axis of rotation 24 and as the rotating assembly 90 rotates about the tube axis of rotation 88.

Figure 6:
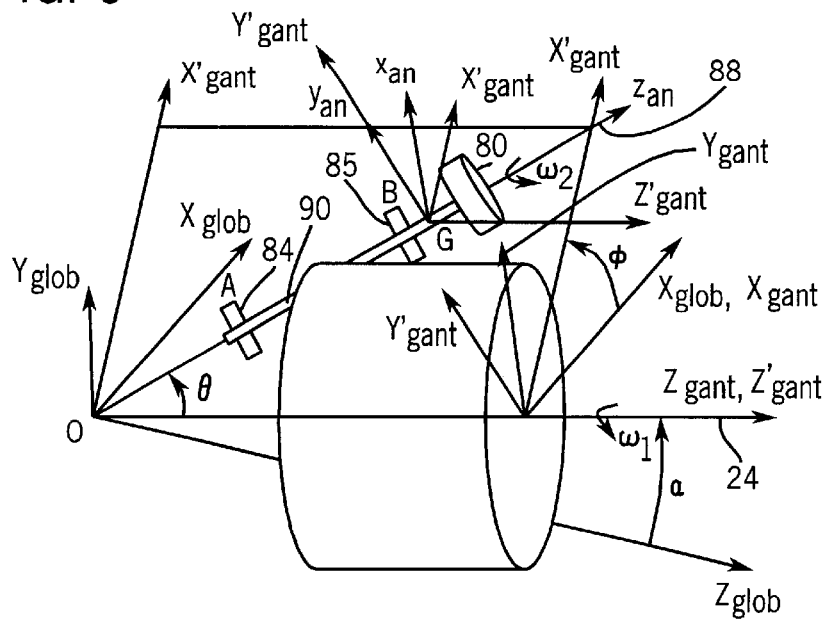
FIGS. 6–8 are diagrams showing the operation of the CT system including the x-ray tube and gantry of FIG. 1.
Figure 7:
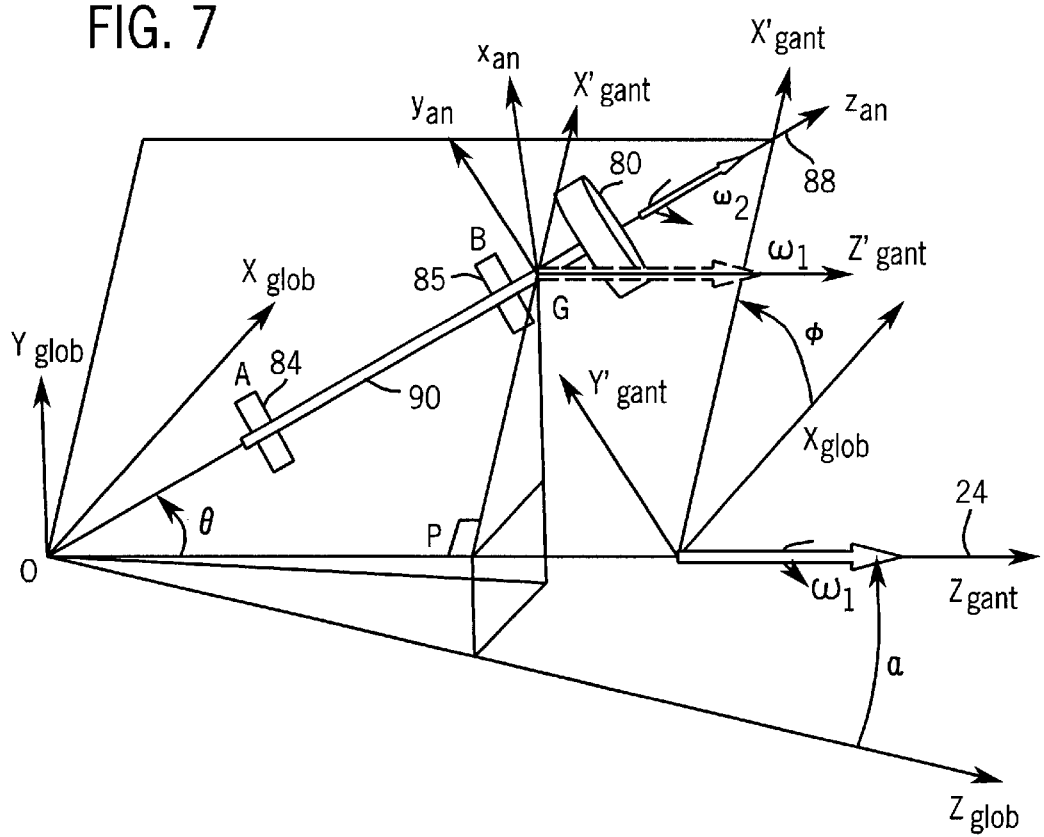
Figure 8:
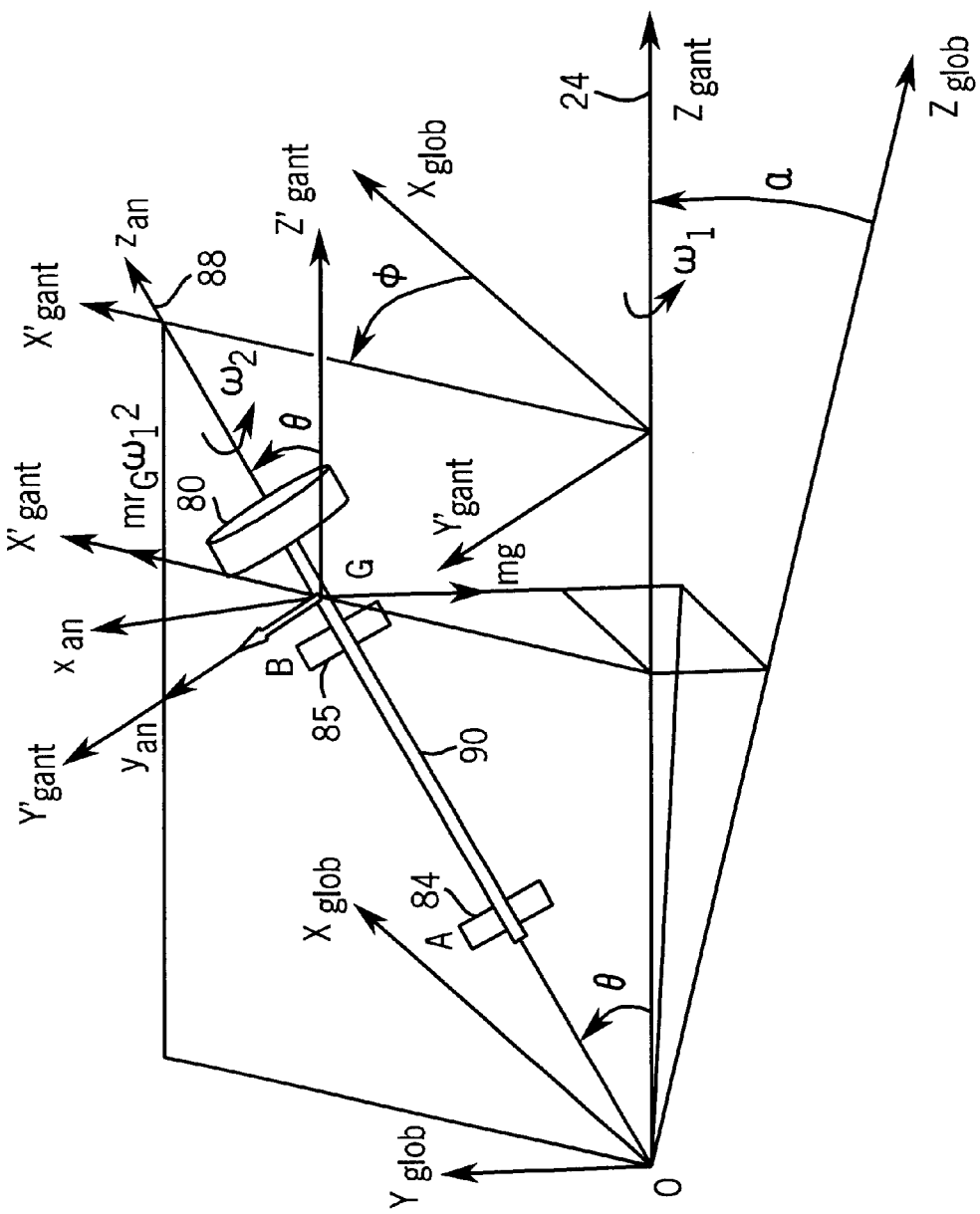

Specifically, and referring now also to FIGS. 6–8, as the gantry 12 rotates about the gantry axis of rotation 24, the x-ray tube 14 also rotates about the gantry axis of rotation 24 since the x-ray tube 14 is mounted to the gantry 12. As this occurs, a centrifugal force is developed due to the rotation of the x-ray tube 14 about the gantry axis of rotation 24. The centrifugal force acts through the center of mass G of the rotating assembly 90 to produce a first moment $\vec{M}_{CF}$ that acts upon the x-ray tube 14.

Likewise, within the x-ray tube 14, the rotating assembly 90 also rotates about the tube axis of rotation 88. Since the rotating assembly 90 is part of the x-ray tube 14, the rotating assembly 90 simultaneously rotates about both the gantry axis of rotation 24 and the tube axis of rotation 88. As shown in FIG. 7, the tube axis of rotation 88 is angularly displaced from the gantry axis of rotation 24 by a tilt angle θ. The rotating assembly 90 therefore precesses. During this precession, the tube axis of rotation 88 circumscribes an outer surface of a portion of a cone as the rotatable assembly 90 rotates about the gantry axis of rotation 24.

The motion of the rotating assembly 90 is somewhat similar to the motion of a top spinning on a floor in that the top rapidly spins about a first axis of rotation while simultaneously, but less rapidly, circumscribing a circle on the floor and thereby spinning about a second axis of rotation. A notable difference is that, in the case of a top, the precession is caused by gravity which produces a moment that acts upon the top. In the case of the x-ray tube 14, the precession is forced by drive motors that drive rotation of the gantry 12 and the rotating assembly 90. Therefore, whereas an input moment (caused by gravity) produces an output precession in the case of a top, an input precession (forced by drive motors) produces an output moment $\vec{M}_G$ in the case of the rotating assembly 90. The output moment $\vec{M}_G$ is a gyroscopic moment that acts upon the x-ray tube 14 and opposes the first moment $\vec{M}_{CF}$. The output moment $\vec{M}_G$ is produced by a pair of forces at the rear and front bearings 84 and 85 that are equal in magnitude but opposite in direction. By suitably choosing a set of operating parameters, it is possible to make the net load on the rear and front bearings 84 and 85 be equal in magnitude. Assuming one continues to rotate the gantry at the same speed, it is therefore possible to lower the load on the front bearing and hence to increase the life of the bearing 85. This arrangement allows for greater control of the relative loading of the rear bearing assembly 84 and the front bearing assembly 85, which in turn allows bearing life to be increased and/or higher speeds to be achieved.

Referring now to FIGS. 6–8, a mathematical description of the forces and moments developed, considering the gyroscopic effect, will now be described. Of course, it should be understood that the following mathematical description merely pertains to a preferred implementation of the invention, and other implementations are possible that would have a different mathematical description. In FIGS. 6–8, the rotating assembly 90 is assumed to be rotating at uniform angular velocity and the X-ray tube 14 rotates with the gantry 12 about the gantry axis 24. Additionally, in the mathematical description that follows, it is assumed that the gantry axis 24 may be tilted.

Table I below contains a description of the parameters shown in FIGS. 6–8.

TABLE I

| | |
|---|---|
| $X_{glob}, Y_{glob}, Z_{glob}$ | Global axes with origin O. Gantry 12 can tilt only about $X_{glob}$. |
| $X_{gant}, Y_{gant}, Z_{gant}$ | Gantry axes with origin O, such that, the gantry 12 rotates about $Z_{gant}$ axis. $X_{gant}$ is parallel to $X_{glob}$. |
| $X'_{gant}, Y'_{gant}, Z'_{gant}$ | Gantry axes with origin G. $Z_{gant}$ and $Z'_{gant}$ have same direction. |
| $x_{an}, y_{an}, z_{an}$ | Anode axes with origin G, such that the anode rotating assembly 90 rotates about $z_{an}$ axis. |
| G | Center of mass of the rotating assembly 90. |
| $\vec{i}_{glob}, \vec{j}_{glob}, \vec{k}_{glob}$ | Triad of unit vectors along $X_{glob}, Y_{glob}, Z_{glob}$, respectively. |
| $\vec{i}'_{gant}, \vec{j}'_{gant}, \vec{k}'_{gant}$ | Triad of unit vectors along $X'_{gant}, Y'_{gant}, Z'_{gant}$, respectively. |
| $\vec{i}_{an}, \vec{j}_{an}, \vec{k}_{an}$ | Triad of unit vectors along $x_{an}, y_{an}, z_{an}$, respectively. |
| A, B | Locations at which the shaft 86 is supported by bearings 84 and 85, respectively. |
| $A_x$ | Reaction perpendicular to the anode axis of rotation 88 ($z_{an}$) and in the plane formed by the anode axis ($z_{an}$) of rotation 88 and the gantry axis of rotation 24 ($Z_{gant}$), i.e., reaction in the $x_{an}$ – direction for bearing 84 at A. |
| $A_y$ | Reaction perpendicular to the anode axis of rotation 88 and also perpendicular to the plane formed by the anode axis of rotation ($z_{an}$) and the gantry axis of rotation 24 ($Z_{gant}$), i.e., reaction in the $y_{an}$ – direction for bearing 84 at A. |
| $A_z$ | Reaction along the anode axis of rotation 88, i.e., reaction in the $z_{an}$ – direction for bearing 84 at A. |
| $B_x$ | Reaction perpendicular to the anode axis of rotation 88 and in the plane formed by the axes of rotation 24 and 88 ($z_{an}$ and $Z_{gant}$), i.e., reaction in the $x_{an}$ – direction for bearing 85 at B. |

TABLE I-continued

| | |
|---|---|
| $B_y$ | Reaction perpendicular to the anode axis of rotation 88 and also perpendicular to the plane formed by the axes of rotation 24 and 88 ($z_{an}$ and $Z_{gant}$), i.e., reaction in the $y_{an}$ – direction for bearing 85 at B. |
| $B_z$ | Reaction along the anode axis of rotation 88, i.e., reaction in the $z_{an}$ – direction for bearing 85 at B. |
| $I_x$ | Mass Moment of inertia of the rotating assembly 90 about $x_{an}$ axis. |
| $I_z$ | Mass Moment of inertia of the rotating assembly 90 about $z_{an}$ axis. |
| $\vec{F}_G$ | Resultant external force acting at point G of the rotating assembly 90. |
| $\vec{H}_G$ | Angular momentum of the rotating assembly 90. |
| $\vec{M}_G$ | Moment vector about G. $\vec{M}_G$ is a gyroscopic moment. |
| $\vec{M}_{CF}$ | Moment vector about G. $\vec{M}_{CF}$ is produced by centrifugal force. |
| a | $z_{an}$ co-ordinate of bearing at A with respect to local reference frame of anode. |
| B | $z_{an}$ co-ordinate of bearing at B with respect to local reference frame of anode. |
| c | $z_{an}$ co-ordinate of focal spot with respect to local reference frame of anode. |
| m | Mass of the rotating assembly 90. |
| g | Magnitude of acceleration due to gravity. |
| l | Distance between bearings = a – b. |
| $r_G$ | Distance of G from gantry $Z_{gant}$ axis. |
| $\alpha$ | Gantry tilt angle, i.e., angle between gantry $Z_{gant}$ axis and global $Z_{glob}$ axis. |
| $\theta$ | Angle between the axes of rotation 24 and 88, i.e., gantry $Z_{gant}$ axis and anode $z_{an}$ axis. |
| $\phi$ | Angular position of tube on the gantry, i.e., angle between gantry $X'_{gant}$ axis and global $X_{glob}$ axis. |
| $\omega_1$ | Angular velocity of the gantry about $Z_{gant}$ axis. |
| $\omega_2$ | Angular velocity of the anode about $z_{an}$ axis. |

It may be noted that parameters with a "$\rightarrow$" sign represent vectors and same parameters represent magnitude if no "$\rightarrow$" is included. Additionally, with respect to the distances a and b, in each case, these distance are measured in a direction that is parallel to the axis of rotation of the anode 88 as shown in FIGS. 6–8. If the bearings 84 and 85 are to the left of the center of gravity G as shown in FIGS. 6–8, then the values of a and b are negative. Moreover, as indicated in Table 1, the parameter $Z_{gant}$ refers to the gantry axis of rotation 24 and the parameter $z_{an}$ refers to the anode axis of rotation 88. In the description that follows, only the parameters $z_{an}$ and $Z_{gant}$ will be used to refer to the axes 24 and 88.

The gantry axis of rotation $Z_{gant}$ and the anode axis of rotation $z_{an}$ are separated by an angle $\theta$ (the tilt angle) at an origin O which is the point of intersection. The gantry $Y_{gant}$ and $Z_{gant}$ axes lie in the $Y_{glob}$ $Z_{glob}$ plane and make an angle $\alpha$ with $Y_{glob}$ and $Z_{gob}$ axes, respectively.

With reference to FIG. 6, the coordinate transformation principle yields the following equations:

$$\begin{Bmatrix} X'_{gant} \\ Y'_{gant} \\ Z'_{gant} \end{Bmatrix} = \begin{bmatrix} \cos\theta & \cos\frac{\pi}{2} & \cos(\frac{\pi}{2}-\theta) \\ \cos\frac{\pi}{2} & \cos 0 & \cos\frac{\pi}{2} \\ \cos(\frac{\pi}{2}+\theta) & \cos\frac{\pi}{2} & \cos\theta \end{bmatrix} \begin{Bmatrix} x_{an} \\ y_{an} \\ z_{an} \end{Bmatrix} \quad (1a)$$

$$\begin{Bmatrix} X_{gant} \\ Y_{gant} \\ Z_{gant} \end{Bmatrix} = \begin{bmatrix} \cos\phi & \cos(\frac{\pi}{2}+\phi) & \cos\frac{\pi}{2} \\ \cos(\frac{\pi}{2}-\phi) & \cos\phi & \cos\frac{\pi}{2} \\ \cos\frac{\pi}{2} & \cos\frac{\pi}{2} & \cos 0 \end{bmatrix} \begin{Bmatrix} X'_{gant} \\ Y'_{gant} \\ Z'_{gant} \end{Bmatrix} \quad (1b)$$

$$\begin{Bmatrix} X_{glob} \\ Y_{glob} \\ Z_{glob} \end{Bmatrix} = \begin{bmatrix} \cos 0 & \cos\frac{\pi}{2} & \cos\frac{\pi}{2} \\ \cos\frac{\pi}{2} & \cos\alpha & \cos(\frac{\pi}{2}-\alpha) \\ \cos\frac{\pi}{2} & \cos(\frac{\pi}{2}+\alpha) & \cos\alpha \end{bmatrix} \begin{Bmatrix} X_{gant} \\ Y_{gant} \\ Z_{gant} \end{Bmatrix} \quad (1c)$$

From the above equations, the relationship between anode coordinates and gantry coordinates can be written as follows:

$$\begin{Bmatrix} X'_{gant} \\ Y'_{gant} \\ Z'_{gant} \end{Bmatrix} = \begin{bmatrix} \cos\theta & 0 & \sin\theta \\ 0 & 1 & 0 \\ -\sin\theta & 0 & \cos\theta \end{bmatrix} \begin{Bmatrix} x_{an} \\ y_{an} \\ z_{an} \end{Bmatrix} \quad (2)$$

The same relationship applies to the corresponding triad of unit vectors as expressed below:

$$\begin{Bmatrix} \vec{i}'_{gant} \\ \vec{j}'_{gant} \\ \vec{k}'_{gant} \end{Bmatrix} = \begin{bmatrix} \cos\theta & 0 & \sin\theta \\ 0 & 1 & 0 \\ -\sin\theta & 0 & \cos\theta \end{bmatrix} \begin{Bmatrix} \vec{i}_{an} \\ \vec{j}_{an} \\ \vec{k}_{an} \end{Bmatrix} \quad (3)$$

Equation (3) can be rewritten as follows:

$$\vec{i}'_{gant}=(\cos\theta)\vec{i}_{an}+(\sin\theta)\vec{k}_{an} \quad \vec{j}'_{gant}=\vec{j}_{an} \quad \vec{k}'_{gant}=(-\sin\theta)\vec{i}_{an}+(\cos\theta)\vec{k}_{an} \quad (4)$$

Also, the relationship between global coordinates and the anode coordinates can be deduced by matrix multiplication as follows:

$$\begin{Bmatrix} X_{glob} \\ Y_{glob} \\ Z_{glob} \end{Bmatrix} = \begin{bmatrix} \cos\phi\cos\theta & -\sin\phi & \cos\phi\sin\theta \\ \sin\phi\cos\theta\cos\alpha-\sin\alpha\sin\theta & \cos\alpha\cos\phi & \sin\phi\sin\theta\cos\alpha+\sin\alpha\cos\theta \\ -\sin\phi\cos\theta\sin\alpha-\cos\alpha\sin\theta & -\sin\alpha\cos\phi & -\sin\phi\sin\theta\sin\alpha+\cos\alpha\cos\theta \end{bmatrix} \begin{Bmatrix} x_{an} \\ y_{an} \\ z_{an} \end{Bmatrix} \quad (5)$$

The same relationship applies to the corresponding triad of unit vectors as expressed below:

$$\begin{Bmatrix} \vec{i}_{glob} \\ \vec{j}_{glob} \\ \vec{k}_{glob} \end{Bmatrix} = \begin{bmatrix} \cos\phi\cos\theta & -\sin\phi & \cos\phi\sin\theta \\ \sin\phi\cos\theta\cos\alpha - \sin\alpha\sin\theta & \cos\alpha\cos\phi & \sin\phi\sin\theta\cos\alpha + \sin\alpha\cos\theta \\ -\sin\phi\cos\theta\sin\alpha - \cos\alpha\sin\theta & -\sin\alpha\cos\phi & -\sin\phi\sin\theta\sin\alpha + \cos\alpha\cos\theta \end{bmatrix} \begin{Bmatrix} \vec{i}_{an} \\ \vec{j}_{an} \\ \vec{k}_{an} \end{Bmatrix} \quad (6)$$

Equation (6) can be rewritten as follows:

$$\vec{i}_{glob} = (\cos\phi\cos\theta)\vec{i}_{an} + (-\sin\phi)\vec{j}_{an} + (\cos\phi\sin\theta)\vec{k}_{an} \quad (7)$$

$$\vec{j}_{glob} = (\sin\phi\cos\theta\cos\alpha - \sin\alpha\sin\theta)\vec{i}_{an} + (\cos\alpha\cos\phi)\vec{j}_{an} +$$
$$(\sin\phi\sin\theta\cos\alpha + \sin\alpha\cos\theta)\vec{k}_{an}$$

$$\vec{k}_{glob} = (-\sin\phi\cos\theta\sin\alpha - \cos\alpha\sin\theta)\vec{i}_{an} + (-\sin\alpha\cos\phi)\vec{j}_{an} +$$
$$(-\sin\phi\sin\theta\sin\alpha + \cos\alpha\cos\theta)\vec{k}_{an}$$

With reference to FIG. 7, the gantry angular velocity $\vec{\omega}_1$ can be written as follows:

$$\vec{\omega}_1 = (-\omega_1 \sin\theta)\vec{i}_{an} + (\omega_1 \cos\theta)\vec{k}_{an} \quad (8)$$

The resultant anode angular velocity $\vec{\omega}$ may then be written as follows:

$$\vec{\omega} = \vec{\omega}_1 + \vec{\omega}_2 = (-\omega_1 \sin\theta)\vec{i}_{an} + (\omega_1 \cos\theta)\vec{k}_{an} + \omega_2\vec{k}_{an} = (-\omega_1 \sin\theta)\vec{i}_{an} + (\omega_1 \cos\theta + \omega_2)\vec{k}_{an} \quad (9)$$

Hence, the anode angular momentum $\vec{H}_G$ can be written as follows:

$$\vec{H}_G = I_x(-\omega_1 \sin\theta)\vec{i}_{an} + I_z(\omega_1 \cos\theta + \omega_2)\vec{k}_{an} \quad (10)$$

Notably, the angular momentum $\vec{H}_G$ is constant (both in magnitude and direction). The resultant gyroscopic moment $\vec{M}_G$ on the rotating assembly 90 about its center of mass G can be written as follows:

$$\vec{M}_G = \frac{d}{dt}(\vec{H}_G) + \vec{\omega}_1 \times \vec{H}_G \quad (11)$$

Therefore, substituting Eqs. (8) and (10) into Eq. (11) yields the following equation:

$$\vec{M}_G = O + (\omega_1 \sin\theta)[I_z(\omega_1\cos\theta + \omega_2) - I_x(\omega_1\cos\theta)]\vec{j}_{an} \quad (12)$$
$$= (\omega_1\sin\theta)[I_z(\omega_1\cos\theta + \omega_2) - I_x(\omega_1\cos\theta)]\vec{j}_{an}$$

From Eq. (12), it is seen that when the tilt angle θ is equal to zero (θ=0), no gyroscopic moment is produced, that is, $\vec{M}_G = O$. When the tilt angle θ is equal to π/2 (θ=π/2), then the gyroscopic moment is non-zero (specifically, $\vec{M}_G = I_z\omega_1\omega_2 \vec{j}_{an}$).

If the anode is considered to be at an arbitrary position on the gantry (see FIG. 8), then the external force $\vec{F}_G$ acting at the center of mass G of the rotating assembly 90 can be written as follows:

$$\vec{F}_G = mr_G\omega_1^2 \vec{i}'_{gant} - mg\vec{j}_{glob} \quad (13)$$

Combining Eqs. (4), (7) and (13) yields the following equations:

$$\vec{F}_G = mr_G\omega_1^2[(\cos\theta)\vec{i}_{an} + (\sin\theta)\vec{k}_{an}] - \quad (14)$$
$$mg[(\sin\phi\cos\theta\cos\alpha - \sin\alpha\sin\theta)\vec{i}_{an} +$$
$$(\cos\alpha\cos\phi)\vec{j}_{an} + (\sin\phi\sin\theta\cos\alpha + \sin\alpha\cos\theta)\vec{k}_{an}]$$

$$\vec{F}_G = [mr_G\omega_1^2\cos\theta - mg(\sin\phi\cos\theta\cos\alpha - \sin\alpha\sin\theta)]\vec{i}_{an} - \quad (15)$$
$$mg(\cos\alpha\cos\phi)\vec{j}_{an} +$$
$$[mr_G\omega_1^2\sin\theta - mg(\sin\phi\sin\theta\cos\alpha + \sin\alpha\cos\theta)]\vec{k}_{an}$$

With regard to Eqs. (14) and (15), the following cases are of particular interest. First, when the angle φ (i.e., angle between gantry axis X'$_{gant}$ and global axis X$_{glob}$) is equal to π/2 (z$_{an}$ axis upwards with respect to Z$_{gant}$ axis in the vertical plane) then the external force $\vec{F}_G$ acting at the center of mass G of the rotating assembly 90 can be written as follows:

$$\vec{F}_G = [mr_G\omega_1^2 \cos\theta - mg\cos(\alpha+\theta)]\vec{i}_{an} + [mr_G\omega_1^2 \sin\theta - mg\sin(\alpha+\theta)]\vec{k}_{an}$$

Second, when the angle φ is equal to −π/2 (z$_{an}$ axis downwards with respect to Z$_{gant}$ axis in the vertical plane) then the external force $\vec{F}_G$ acting at the center of mass G of the rotating assembly 90 can be written as follows:

$$\vec{F}_G = [mr_G\omega_1^2 \cos\theta + mg\cos(\theta-\alpha)]\vec{i}_{an} + [mr_G\omega_1^2 \sin\theta + mg\sin(\theta-\alpha)]\vec{k}_{an}$$

Assuming $\vec{A}$ and $\vec{B}$ are defined as the reaction forces at the bearings located at A and B, respectively, and the sum of all the forces must be zero, then the following equation must be true:

$$\vec{A} + \vec{B} + \vec{F}_G = O \quad (16)$$

Substituting for $\vec{F}_G$ from Eq. (15) yields the following equations:

$$A_x + B_x + [mr_G\omega_1^2 \cos\theta - mg(\sin\phi\cos\theta\cos\alpha - \sin\alpha\sin\theta)] = O \quad (17a)$$

$$A_y + B_y - mg(\cos\alpha\cos\phi) = 0 \quad (17b)$$

$$A_z + B_z + [mr_G\omega_1^2 \sin\theta - mg(\sin\phi\sin\theta\cos\alpha + \sin\alpha\cos\theta)] = O \quad (17c)$$

Computing moments about the center of gravity G yields the following equation:

$$(a\vec{k}_{an} \times \vec{A}) + (b\vec{k}_{an} \times \vec{B}) + \vec{M}_G = O \quad (18)$$

Substituting for $\vec{M}_G$ from Eq. (12) yields the following equations:

$$aA_x + bB_x + (\omega_1 \sin\theta)[I_z(\omega_1 \cos\theta + \omega_2) - I_x(\omega_1 \cos\theta)] = O \quad (19a)$$

$$aA_y + bB_y = O \quad (19b)$$

Solving for $A_x$ and $B_x$ simultaneously from Eqs. (17a) and (19a) yields the following equations:

$$A_x = \frac{-(\omega_1 \sin\theta)[I_z(\omega_1 \cos\theta + \omega_2) - I_x \omega_1 \cos\theta]}{(a-b)} \quad (20a)$$
$$+ \frac{mb[r_G \omega_1^2 \cos\theta - g(\sin\phi\cos\theta\cos\alpha - \sin\alpha\sin\theta]}{(a-b)}$$

$$B_x = \frac{(\omega_1 \sin\theta)[I_z(\omega_1 \cos\theta + \omega_2) - I_x \omega_1 \cos\theta]}{(a-b)} \quad (20b)$$
$$- \frac{ma[r_G \omega_1^2 \cos\theta - g(\sin\phi\cos\theta\cos\alpha - \sin\alpha\sin\theta)]}{(a-b)}$$

Solving for $A_y$ and $B_y$ simultaneously from Eqs. (17b) and (19b) yields the following equations:

$$A_y = \frac{-mbg\cos\alpha\cos\phi}{(a-b)} \quad (21a)$$

$$B_y = \frac{mag\cos\alpha\cos\phi}{(a-b)} \quad (21b)$$

Figure 9A:
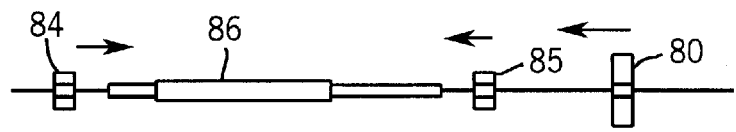
FIGS. 9A–9B schematically show the assembly of the anode assembly of FIG. 3 as pertains to axial forces that are developed on front and rear bearings of the anode assembly.
Figure 9B:
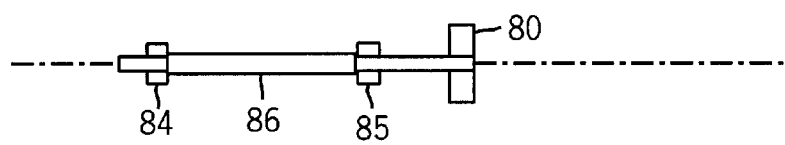

It may be noted that there is only one equation (Eq. 17c) and there are two variables ($A_z$ and $B_z$). For purposes of considering the axial forces applied to the bearings, the following considerations may be kept in mind. First, the worst case is when $A_z = 0$ or $B_z = 0$, that is, when all the axial force is applied to one bearing. Second, if one bearing is a deep groove ball bearing and the other bearing is an angular contact bearing, then all the axial force will be borne by angular contact bearing only. Third, for the purpose of assembly, if there is a stepped shaft, as illustrated in FIGS. 9A–9B, a small amount of axial "play" should be maintained to allow rotation (otherwise the assembly may become jammed). In this case, the axial force is applied to only one bearing.

In view of the above, one of the two following sets of conditions will be true:

$$A_z = -mr_G \omega_1^2 \sin\theta + mg(\sin\phi \sin\theta \cos\alpha + \sin\alpha \cos\theta) \quad (22a)$$

$$B_z = 0 \quad (22b)$$

or $$A_z = 0 \quad (23a)$$

$$B_z = -mr_G \omega_1^2 \sin\theta + mg(\sin\phi \sin\theta \cos\alpha + \sin\alpha \cos\theta) \quad (23b)$$

For the ongoing analysis, consider Eqs. (23a)–(23b) will be considered.

Figure 10:
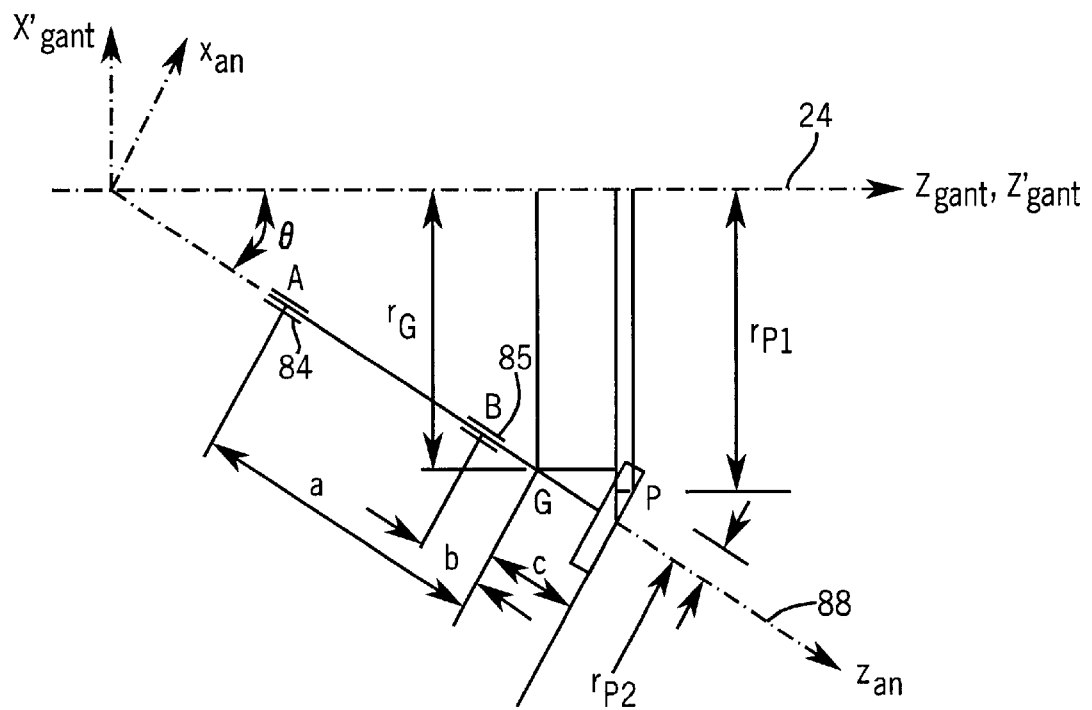
FIG. 10 is another diagram showing the operation of the CT system of FIG. 1.

To examine geometrical constraints, assume that $r_{P1}$ is the radius of the point of incidence with respect to the gantry $Z_{gant}$ axis, $r_{P2}$ is the point of incidence with respect to the anode $z_{an}$ axis, and c is the distance of the center of the extreme anode surface from the center of mass of the anode. It may then be noted that the point of incidence lies on the plane formed by gantry $Z_{gant}$ axis and anode $z_{an}$ axis. Thus, for the purpose of analysis, this plane may be considered as shown in FIG. 10. From FIG. 10.

$$r_G + c \sin\theta = r_{P1} + r_{P2} \cos\theta \quad (24)$$

Hence, $$r_G = r_{P1} + r_{P2} \cos\theta - c \sin\theta \quad (25)$$

Referring again to Eqs. (20a)–(20b) and (21a)–(21b), it may be noted that the effects of gravity are relatively minor as compared to the effects of the moments $M_G$ and $M_{CF}$, especially at higher speeds. If the effects of gravity are ignored in Eqs. (20a)–(20b) and (21a)–(21b), then the force in the y-direction is equal to zero (Eqs. (21a)–(21b)) and Eqs. (20a)–(20b) may be simplified as follows:

$$A_x = \frac{-(\omega_1 \sin\theta)[I_z(\omega_2 + \omega_1 \cos\theta) - I_x \omega_1 \cos\theta] + mb[r_G \omega_1^2 \cos\theta]}{(a-b)} \quad (26a)$$

$$B_x = \frac{(\omega_1 \sin\theta)[I_z(\omega_2 + \omega_1 \cos\theta) - I_x \omega_1 \cos\theta] + ma[r_G \omega_1^2 \cos\theta]}{(a-b)} \quad (26b)$$

With respect to the force $A_X$ applied to the rear bearing assembly 84, this force can be broken down into two components as follows:

$$A_{X1} = \frac{mb[r_G \omega_1^2 \cos\theta]}{(a-b)} \quad (27a)$$

$$A_{X2} = \frac{-(\omega_1 \sin\theta)[I_z(\omega_2 + \omega_1 \cos\theta) - I_x \omega_1 \cos\theta]}{(a-b)} \quad (27b)$$

where $A_{X1}$ is the load applied to the rear bearing assembly 84 due to the centrifugal force in reaction to centripetal acceleration and $A_{X2}$ is the load applied to the rear bearing assembly 84 due to the gyroscopic moment $M_G$.

Likewise, with respect to the force $F_B$ applied to the front bearing assembly 85, this force can be broken down into two components as follows:

$$B_{X1} = \frac{-ma[r_G \omega_1^2 \cos\theta]}{(a-b)} \quad (28a)$$

$$B_{X2} = \frac{(\omega_1 \sin\theta)[I_z(\omega_2 + \omega_1 \cos\theta) - I_x \omega_1 \cos\theta]}{(a-b)} \quad (28b)$$

where $B_{X1}$ is the load applied to the front bearing assembly 85 due to the centrifugal force and $B_{X2}$ is the load applied to the front bearing assembly 85 due to the gyroscopic moment $M_G$.

Based on how the x-ray tube 14 is mounted to the gantry (that is, depending on the tilt angle), it is possible to adjust the relative loading of the rear and front bearing assemblies 84 and 85. The parameters of Eqs. (26a)–(26b) can be optimized based on the application to achieve a particular gantry speed or to achieve a particular relative loading between the rear and front bearings 84 and 85. Once the remaining parameters of Eqs. (26a)–(26b) are decided upon, Eqs. (26a)–(26b) can be solved to derive the correct tilt angle. If desired, Eqs. (20a)–(20b) and (21a)–(21b) may be used instead, although the effects of gravity are relatively minor as compared to the effects of the centrifugal force and gyroscopic moment (as previously noted). Eqs. (22a)–(22b), (23a)–(23b), (24) and (25) may be taken into account in connection with axial loading when constructing the bearing assemblies 84 and 85. In this regard, it may be noted that the bearing assemblies 84 and 85 may need to be constructed to handle additional load in the axial direction due to the tilting of the anode axis relative to the gantry axis.

Figure 11:
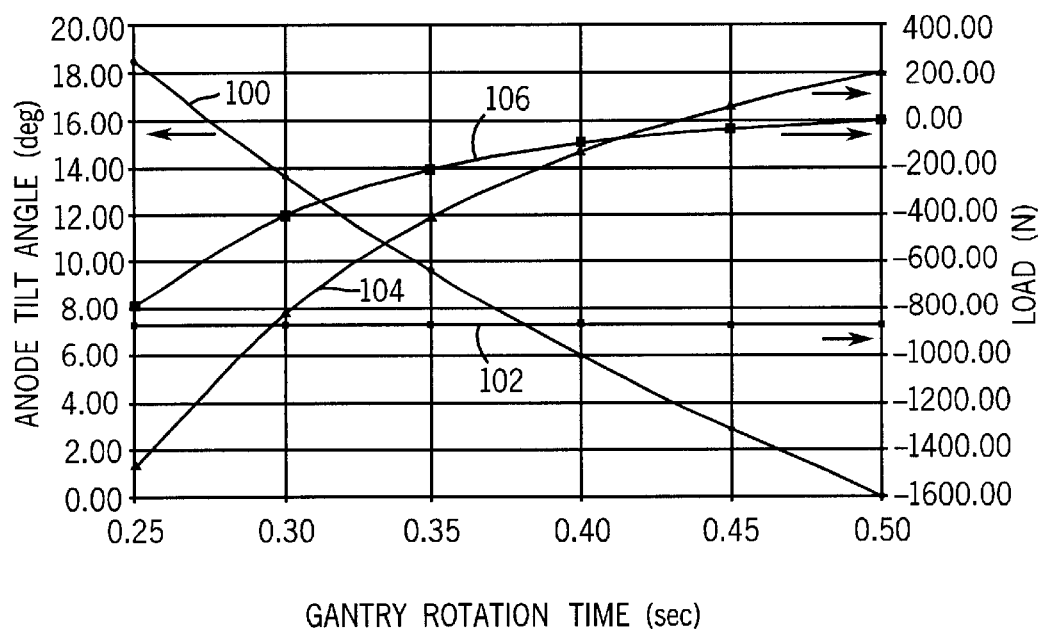
FIG. 11 is a graph of the anode tilt angle required to maintain a particular front bearing load at different gantry rotation speeds.

Referring now to FIG. 11, FIG. 11 is a graph of the anode tilt angle θ required to maintain constant front bearing load as a function of gantry rotation time for an exemplary anode construction. Curve 100 is the anode tilt angle θ (in degrees, left axis), curve 102 is the radial load (in Newtons, right axis) applied to the front bearing 85, curve 104 is the radial load (in Newtons, right axis) applied to the front bearing 84, and curve 106 is the axial load (in Newtons, right axis)

applied to the rear bearing 85. As shown in FIG. 11, as gantry rotation time decreases (or gantry speed increases), the tilt angle θ can be increased to increase the magnitude of the loading experienced by the rear bearing assembly 84. This allows the total loading experienced by the bearings 84 and 85 to increase without exceeding the design limit of bearing 85.

The tilt angle preferably has a magnitude which is greater than 2° and less than 70°. For example, the tilt may have a magnitude which is greater than 5° and less than 50°, or more preferably less than 20°. According to this arrangement, it is possible to achieve a more balanced loading between the rear bearing assembly 84 and the front bearing assembly 85, rather than having the front bearing assembly bear most of the load. For example, the loading that is experienced by the rear bearing assembly 84 may be one tenth (i.e., an order of magnitude less than) that at the front bearing assembly 85. Preferably, the loading is experienced by the rear bearing assembly 84 is at least half or three-quarters as large as loading experienced by the front bearing assembly 85. Most preferably, the rear bearing 84 and the front bearing 85 are approximately equally loaded. In FIG. 11, equal loading occurs at a gantry rotation time of about 0.295 sec (or rotation speed of about 3.4 Hz) with a tilt angle of about 14°.

Figure 12A:
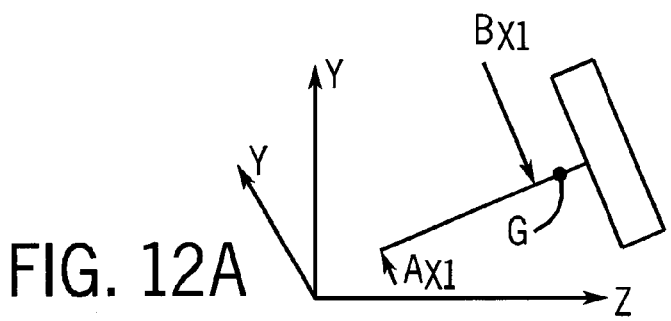
FIGS. 12A–12C show forces developed during the operation of the CT system of FIG. 1.
Figure 12B:
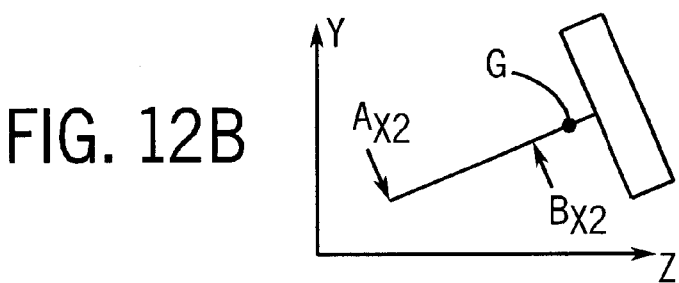
Figure 12C:
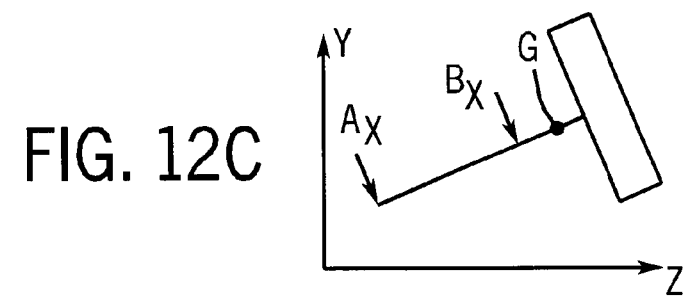

Referring now to FIGS. 12A–12C, FIGS. 12A–12C pictorially describe how the balanced loading is achieved. Initially, it may be noted that the vectors shown in FIGS. 12A–12C are not shown in the positive direction but in the actual direction based on the geometry shown. FIG. 12A shows the forces $A_{X1}$ and $B_{X1}$ applied to the bearing shaft in the location of bearings 84 and 85 as a result of the centrifugal force. As shown, the force $B_{X1}$ is much larger than the force $A_{X1}$, which is also in the opposite direction. FIG. 12B shows the forces $A_{X2}$ and $B_{X2}$ applied to the bearing shaft at bearings 84 and 85, respectively, as a result of the gyroscopic moment $M_G$. As shown in FIG. 12B, the force $B_{X2}$ opposes the force $B_{X1}$, and the reduction in force applied to the bearing 85 is compensated by an increase in the force $A_{X2}$ applied at the bearing 84. As a result, as shown in FIG. 12C, the net force $A_X$ applied to the bearing 84 is approximately equal to the net force $B_X$ applied to the bearing 85.

Figure 13A:
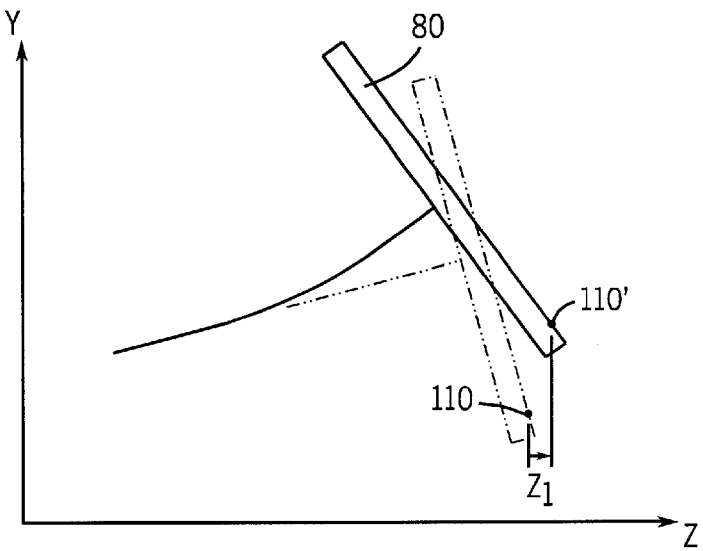
FIGS. 13A–13C show the operation of the forces of FIGS. 12A–12C to reduce anode deflection and thereby improve imaging.
Figure 13B:
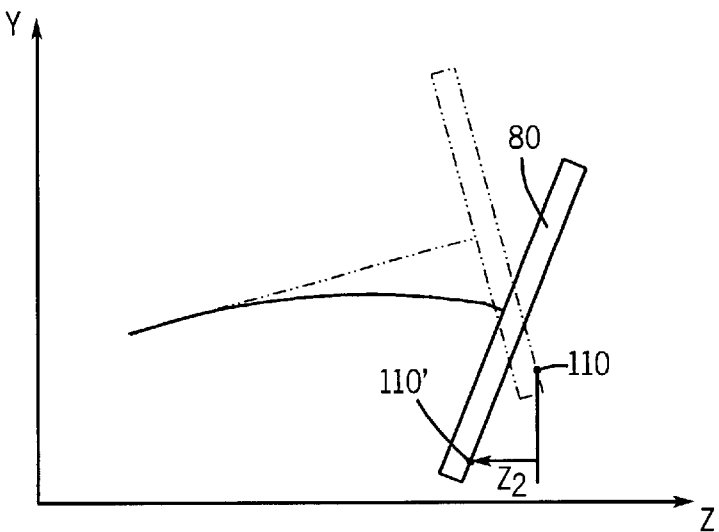
Figure 13C:
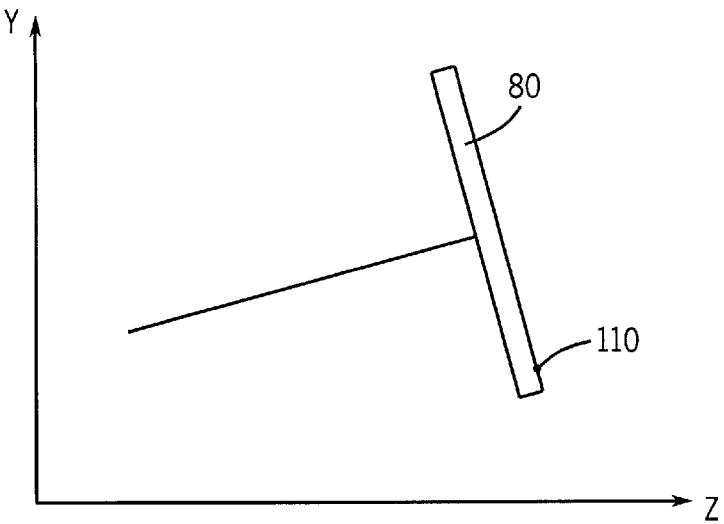

Referring now to FIGS. 13A–13C, operation of the above-described to improve imaging is shown. FIG. 13A shows deflection of the target 80 due to centrifugal force. During scanning, the centrifugal force on the target 80 causes the target 80 to deflect outward away from the gantry rotation axis a distance of $Z_1$. This causes the focal spot 110 of the x-ray beam that is reflected by the target 80 to move in the z-direction to a position 110'. As shown in FIG. 13B, the gyroscopic moment $M_G$ applies an opposing force which causes the target 80 to deflect in the opposite direction a distance of $Z_2$. Therefore, as shown in FIG. 13C, the net deflection is greatly reduced and approaches zero. Because the net deflection is greatly reduced by the production of the gyroscopic moment $M_G$, movement of the focal spot 110 is greatly reduced. The tilted rotating assembly 90 therefore serves not just to emit the x-rays, but also to gyroscopically stabilize the focal spot 110 of the x-ray beam. The benefit of the two counter-balancing forces is that the focal spot 110 moves much less in the z-direction and hence under all scanning procedures, the focal spot 110 remains much more fixed with respect to the detector. This stability in the focal spot position leads to better image quality.

While the embodiments illustrated in the Figures and described above are presently preferred, it should be understood that these embodiments are offered by way of example only. The invention is not limited to a particular embodiment, but extends to various modifications, combinations, and permutations that nevertheless fall within the scope and spirit of the appended claims.

What is claimed is:

1. A computed tomography system comprising:
   (A) a gantry, the gantry rotating about a gantry axis of rotation;
   (B) an x-ray tube, the x-ray tube being mounted to the gantry, the x-ray tube comprising a rotatable assembly having a tube axis of rotation, the tube axis of rotation being angularly displaced from the gantry axis of rotation by a tilt angle;
   wherein rotation of the x-ray tube about the gantry axis of rotation causes a centrifugal force to be applied to the rotatable assembly, the centrifugal force producing a first moment; and
   wherein rotation of the rotatable assembly about the tube axis of rotation produces a second moment that opposes the first moment.

2. A computed tomography system according to claim 1, wherein the x-ray tube further comprises a first bearing assembly and a second bearing assembly;
   wherein the second bearing assembly is located along said tube axis of rotation between said the first bearing assembly and a center of gravity of the rotatable assembly; and
   wherein, during rotation of the x-ray tube about the gantry axis of rotation and during the rotation of the rotatable assembly about the tube axis of rotation, the first and second bearing assemblies experience approximately equal loading.

3. A computed tomography system according to claim 1, wherein the x-ray tube further comprises a first bearing assembly and a second bearing assembly;
   wherein the second bearing assembly is located along the tube axis of rotation between the first bearing assembly and a center of gravity of the rotatable assembly; and
   wherein, during rotation of the x-ray tube about said gantry axis of rotation and during the rotation of the rotatable assembly about said the tube axis of rotation, the first bearing assembly experiences loading that is at least one tenth as large as loading experienced by the second bearing assembly.

4. A computed tomography system according to claim 3 wherein, during rotation of the x-ray tube about the gantry axis of rotation and during the rotation of the rotatable assembly about the tube axis of rotation, the first bearing assembly experiences loading that is at least three-quarters as large as loading experienced by the second bearing assembly.

5. A computed tomography system according to claim 4, further comprising an x-ray detector, the detector being mounted to the gantry, and wherein the x-ray tube emits x-rays that are detected by the x-ray detector while the rotatable assembly rotates about the tube axis of rotation to produce the second moment that opposes the first moment.

6. A computed tomography system according to claim 1, wherein the tilt angle has a magnitude which is greater than 2°.

7. A computed tomography system according to claim 1, wherein said the tilt angle has a magnitude which is greater than 5°.

8. A computed tomography system according to claim 1, wherein the tilt angle has a magnitude which is greater than 5° and less than 20°.

9. A computed tomography system according to claim 1,
wherein the gantry rotates at a gantry rotational speed; and
wherein the second moment is a gyroscopic moment that is produced by precession of the rotatable assembly, the precession occurring by way of the rotation of the x-ray tube about the gantry axis of rotation and the rotation of the rotatable assembly about the tube axis of rotation, the tube axis of rotation of the rotatable assembly circumscribing an outer surface of a portion of a cone as the rotatable assembly rotates about the gantry axis of rotation.

10. The system of claim 1, wherein loads on a first set of bearings of the x-ray tube and a second set of bearings of the x-ray tube are closer to being equal when the x-ray tube axis of rotation is angularly displaced from the gantry axis of rotation by the tilt angle than when the x-ray tube axis of rotation is not angularly displaced from the gantry axis of rotation.

11. The system of claim 1, wherein the tilt angle causes the second moment to gyroscopically stabilize the system.

12. The system of claim 1, wherein the x-ray tube is configured to emit x-rays for use in acquiring medical images of a human patient.

13. The system of claim 1, wherein the tilt angle causes the x-ray tube to precess at a rate that is synchronized to the rate of rotation of the gantry.

14. A method of operating a computed tomography system comprising:
producing a first moment that acts upon an x-ray tube, the first moment being produced by rotation of a gantry about a gantry axis of rotation at a gantry rotational speed the x-ray tube being mounted to the gantry;
producing a second moment that acts upon the x-ray tube while the first moment is being produced, the second moment being produced by rotation of a rotating assembly of the x-ray tube about a tube axis of rotation, the tube axis of rotation being angularly displaced from the gantry axis of rotation by a tilt angle;
wherein the second moment is a gyroscopic moment that is produced by precession of the rotatable assembly, the precession occurring by way of the rotation of the x-ray tube about the gantry axis of rotation and the rotation of the rotatable assembly about the tube axis of rotation, and the tube axis of rotation of the rotatable assembly circumscribing an outer surface of a portion of a cone as the rotatable assembly rotates about the gantry axis of rotation.

15. A method according to claim 14, wherein said the tilt angle has a magnitude which is greater than 2° and less than 70°.

16. A method according to claim 14, wherein the tilt angle has a magnitude which is greater than 5° and less than 20°.

17. A method according to claim 14, wherein said the tilt angle has a magnitude which is greater than 2°.

18. A method according to claim 14, further comprising receiving a human patient inside the gantry, and wherein the x-ray tube emits x-rays that pass through the human patient and are received at a detector during the producing steps.

19. A method according to claim 14, wherein the step of producing the second moment stabilizes the focal spot position of an x-ray beam of the x-ray tube.

20. A method of operating a computed tomography system comprising:
producing a first moment that acts upon an x-ray tube, the first moment being produced by rotation of a gantry about a gantry axis of rotation, the x-ray tube being mounted to the gantry;
producing a second moment that acts upon the x-ray tube while the first moment is being produced, said the second moment being produced by rotation of a rotating assembly of the x-ray tube about a tube axis of rotation, the tube axis of rotation being angularly displaced from the gantry axis of rotation by a tilt angle; and
wherein said the tilt angle has a magnitude which is greater than 2°.

21. The system of claim 20, wherein the x-ray tube is configured to emit x-rays for use in acquiring medical images of a human patient.

22. A computed tomography system comprising:
(A) a gantry, gantry rotating about a gantry axis of rotation at a gantry rotational speed;
(B) an x-ray tube the x-ray tube being mounted to said gantry, said the x-ray tube comprising
(1) a vacuum vessel;
(2) an anode assembly, the anode assembly being disposed in the vacuum vessel, the anode assembly including
(a) a first bearing assembly;
(b) a second bearing assembly;
(c) a rotatable assembly including
(i) a rotatable shaft, the rotatable shaft being rotatably mounted within the vacuum vessel by way of the first and second bearing assemblies, the rotatable shaft defining a tube axis of rotation, the tube axis of rotation being angularly displaced from the gantry axis of rotation by a tilt angle;
(ii) a target, the target being coupled to said the shaft and rotating with the shaft, the target and the first bearing assembly being disposed on opposite sides of the second bearing assembly along the tube axis of rotation; and
(3) a cathode assembly, the cathode assembly being disposed in the vacuum vessel at a distance from the anode assembly, the cathode assembly being configured to emit electrons that bombard the target to produce x-rays;
wherein a center of gravity of the rotatable assembly is located between (a) the target and (b) the first and second bearing assemblies;
wherein rotation of the rotatable assembly about the gantry axis of rotation causes a centrifugal force to be applied to the rotatable assembly, the centrifugal force producing a first moment; and
wherein rotation of the rotatable assembly about the tube axis of rotation produces a second moment that opposes the first moment.

23. A computed tomography system according to claim 22,
wherein the gantry rotates at a gantry rotational speed; and
wherein the second moment is a gyroscopic moment that is produced by precession of the rotatable assembly, the precession occurring by way of the rotation of the x-ray tube about the gantry axis of rotation and the rotation of the rotatable assembly about the tube axis of rotation, the tube axis of rotation of the rotatable assembly circumscribing an outer surface of a portion of a cone as the rotatable assembly rotates about the gantry axis of rotation.

24. A computed tomography system according to claim 22, wherein tilt angle has a magnitude which is greater than 2° and less than 50°.

25. A computed tomography system according to claim 22, wherein the tilt angle has a magnitude which is greater than 5° and less than 20°.

26. A computed tomography system according to claim 22, wherein, during rotation of the x-ray tube about said the gantry axis of rotation and during the rotation of the rotatable assembly said the tube axis of rotation, the first bearing assembly experiences loading that is at least three-quarters as large as loading experienced by the second bearing assembly.

27. A computed tomography system according to claim 22, further comprising an x-ray detector, the detector being mounted to the gantry, and wherein the x-ray tube emits x-rays that are detected by the x-ray detector while the rotatable assembly rotates said the tube axis of rotation to produce the second moment that opposes the first moment.

28. The system of claim 22, wherein the x-ray tube is configured to emit x-rays for use in acquiring medical images of a human patient.

29. A computed tomography system comprising:
(A) means for generating x-rays, the x-rays being emitted from the means for generating in the form of an x-ray beam having a focal spot, and the means for generating including a means for gyroscopically stabilizing a position of said focal spot of the x-ray beam; and p1 (B) means for detecting the x-rays generated by the means for generating.

30. The system of claim 29, wherein the means for generating x-rays is configured to emit x-rays for use in acquiring medical images of a human patient.

31. A computed tomography system comprising:
(A) a gantry, the gantry rotating about a gantry axis of rotation;
(B) an x-ray tube the x-ray tube being mounted to said the gantry, said the x-ray tube comprising a rotatable assembly having a tube axis of rotation, the tube axis of rotation being angularly displaced from the gantry axis of rotation by a tilt angle;

wherein rotation of the x-ray tube about the gantry axis of rotation causes a centrifugal force to be applied to the rotatable assembly; and wherein rotation of the rotatable assembly about the tube axis of rotation produces a gyroscopic moment that results in an additional force being applied to the rotatable assembly that opposes the centrifugal force.

32. The system of claim 31, wherein the x-ray tube is configured to emit x-rays for use in acquiring medical images of a human patient.

33. A method of operating a tomography system, comprising:
generating x-rays, the x-rays being emitted from an x-ray generator in the form of an x-ray beam having a focal spot;
wherein generating x-rays includes gyroscopically stabilizing a position of the focal spot of the x-ray beam.

34. A method of operating a tomography system, comprising:
rotating a gantry along a gantry axis of rotation; and
rotating an x-ray tube along an x-ray tube axis of rotation that is angularly displaced from the gantry axis of rotation by a tilt angle;
wherein loads on a first set of bearings of the x-ray tube and a second set of bearings of the x-ray tube are closer to being equal when the x-ray tube axis of rotation is angularly displaced from the gantry axis of rotation by the tilt angle than when the x-ray tube axis of rotation is not angularly displaced from the gantry axis of rotation.

35. The method of claim 34, wherein the loads on the first set of bearings of the x-ray tube and the second set of bearings of the x-ray tube are about equal when the x-ray tube axis of rotation is angularly displaced from the gantry axis of rotation by the tilt angle.

36. A method according to claim 34, wherein the tilt angle has a magnitude which is greater than 2° and less than 70°.

37. A method according to claim wherein the tilt angle has a magnitude which is greater than 5° and less than 20°.

38. A method according to claim 34, wherein the tilt angle has a magnitude which is greater than 2°.

* * * * *

UNITED STATES PATENT AND TRADEMARK OFFICE
CERTIFICATE OF CORRECTION

PATENT NO. : 6,704,392 B2
DATED : March 9, 2004
INVENTOR(S) : Thomas G. Ebben and Douglas J. Snyder It is certified that error appears in the above-identified patent and that said Letters Patent is hereby corrected as shown below:

Column 14,
Lines 26 and 42, please delete "said".

Column 15,
Line 34, after "speed" please insert -- , --.
Line 55, please delete "said".

Column 16,
Lines 4, 10, 29 and 35, please delete "said".
Line 26, after the first appearance of "a gantry," please insert -- the --.
Line 28, after the first appearance of "x-ray tube" please insert -- , --.

Column 17,
Lines 8, 9 and 37, please delete "said".
Line 4, after "assembly" please insert -- about --.
Line 18, after "rotates" please insert -- about --.
Line 28, please delete "p1".
Line 37, after the first appearance of "x-ray tube" please insert -- , --.

Signed and Sealed this

Twenty-ninth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO.   : 6,704,392 B2
DATED        : March 9, 2004
INVENTOR(S)  : Thomas G. Ebben and Douglas J. Snyder Page 1 of 1

It is certified that error appears in the above-identified patent and that said Letters Patent is hereby corrected as shown below:

Column 14,
Lines 26 and 42, please delete "said".

Column 15,
Line 34, after "speed" please insert -- , --.
Line 55, please delete "said".

Column 16,
Lines 4, 10, 19 and 35, please delete "said".
Line 16, after the first appearance of "a gantry," please insert -- the --.
Line 18, after the first appearance of "x-ray tube" please insert -- , --.

Column 17,
Lines 8, 9 and 37, please delete "said".
Line 4, after "assembly" please insert -- about --.
Line 18, after "rotates" please insert -- about --.
Line 28, please delete "p1".
Line 37, after the first appearance of "x-ray tube" please insert -- , --.

This certificate supersedes Certificate of Correction issued June 29, 2004

Signed and Sealed this

Tenth Day of May, 2004

JON W. DUDAS
*Director of the United States Patent and Trademark Office*

UNITED STATES PATENT AND TRADEMARK OFFICE
CERTIFICATE OF CORRECTION

PATENT NO. : 6,704,392 B2  Page 1 of 1
DATED : March 9, 2004
INVENTOR(S) : Thomas G. Ebben and Douglas J. Snyder It is certified that error appears in the above-identified patent and that said Letters Patent is hereby corrected as shown below:

Column 14,
Lines 26 and 42, delete "said".

Column 15,
Line 34, after "speed" insert -- , --.
Line 55, delete "said".

Column 16,
Lines 4, 10, 29 and 35, delete "said".
Line 26, after the first appearance of "a gantry," insert -- the --.
Line 28, after the first appearance of "x-ray tube" insert -- , --.

Column 17,
Lines 8, 10, 18 and 37, delete "said".
Line 10, after "assembly" insert -- about --.
Line 18, after "rotates" insert -- about --.
Line 28, delete "p1".
Line 37, after the first appearance of "x-ray tube" insert -- , --.

This certificate supersedes Certificate of Correction issued June 29, 2004 and May 10, 2005.

Signed and Sealed this

Ninth Day of May, 2006

JON W. DUDAS
*Director of the United States Patent and Trademark Office*